US006221023B1

United States Patent
Matsuba et al.

(10) Patent No.: US 6,221,023 B1
(45) Date of Patent: Apr. 24, 2001

(54) SENSOR FOR INTRA-CORPOREAL MEDICAL DEVICE AND A METHOD OF MANUFACTURE

(75) Inventors: Tomoyoshi Matsuba; Hitoshi Iwata, both of Aichi-ken (JP)

(73) Assignee: Kabushiki Kaisha Tokai Rika Denki Seisakusho, Aichi-Ken (JP)

( * ) Notice: Subject to any disclaimer, the term of this patent is extended or adjusted under 35 U.S.C. 154(b) by 0 days.

(21) Appl. No.: 08/781,936

(22) Filed: Dec. 2, 1996

(30) Foreign Application Priority Data

Dec. 1, 1995 (JP) .................................................. 7-314327

(51) Int. Cl.[7] ........................................................ A61B 5/02
(52) U.S. Cl. ........................... 600/486; 600/488; 600/561
(58) Field of Search .................................. 600/486, 488, 600/561

(56) References Cited

U.S. PATENT DOCUMENTS

| 2,959,056 | * | 11/1960 | Traite et al. | 600/488 |
| 3,550,583 | * | 12/1970 | Chiku | 600/488 |
| 3,553,625 | * | 1/1971 | Stedman | 600/488 |
| 3,831,588 | * | 8/1974 | Rindner | 600/488 |
| 4,274,423 | * | 6/1981 | Mizuno et al. | 600/488 |
| 4,554,927 | * | 11/1985 | Fussell | 600/486 |
| 4,846,191 | * | 7/1989 | Brockway et al. | 600/486 |
| 4,886,070 | * | 12/1989 | Demarest | 600/488 |
| 5,353,800 | * | 10/1994 | Pohndorf et al. | 600/486 |

FOREIGN PATENT DOCUMENTS 6-190050    7/1994  (JP) .

* cited by examiner

Primary Examiner—Robert L. Nasser
(74) Attorney, Agent, or Firm—Sheridan Ross P.C.

(57) ABSTRACT

A sensor mounted on the distal end of an intra-corporeal catheter detects pressure applied thereto. The sensor includes a chip that is deformable in accordance with pressure applied thereto, strain gauges mounted on the chip, a sensing plate, a projection, a cap and a tube. A cover covers the chip, the sensing plate, the projection and the cap and gives a smooth tapered shape to the catheter's distal end. The projection and the cap transmit pressure applied to the catheter's distal end to the sensing plate and tilt the sensing plate in accordance with the pressure. The strain gauges issue detection signals according to the degree and the direction of the tilting. The pressure applied to the catheter's distal end is detected based on the issued signals.

29 Claims, 8 Drawing Sheets

SENSOR FOR INTRA-CORPOREAL MEDICAL DEVICE AND A METHOD OF MANUFACTURE

BACKGROUND OF THE INVENTION

1. Field of the Invention

The present invention relates to a sensor mounted on an intra-corporeal medical device. More particularly, the present invention relates to a sensor mounted on the distal end of a catheter for detecting pressure acting thereon.

2. Description of the Related Art

Catheters and endoscopes are medical devices that are inserted into passageways in the human body such as blood vessels to perform medical treatment. These devices typically include a tube, which is inserted into the body, and a manipulator for manipulating the tube from outside the patient's body. The tube is inserted into an intra-corporeal passageway, such as a blood vessel. Then, the doctor uses the manipulator to guide the distal end of the tube to a desirable point, where he or she performs measuring (e.g., measurement of the blood pressure) or medical treatment (e.g. vasodilation).

The intra-corporeal passageways are curved and branched and their diameters vary at different locations. In addition, obstacles such as a thrombus may narrow the passageways. The doctor therefore uses the manipulator to bend the tube in order to guide the tube's distal end through branches.

When operating a prior art catheter, the doctor senses an increase in the insertion resistance of the tube based on the tactile feeling from the catheter and thus senses curved parts, narrow parts and obstacles in the passageway. This allows the doctor to determine the advancing direction of the catheter, The doctor needs to be experienced and must sometime use his or her instincts in manipulating the catheter's distal end. Further, judging the direction of the insertion pressure is often difficult.

To solve the above drawback, it has been proposed that a sensor be mounted on the distal end of a tube for detecting the magnitude and direction of pressure applied to the sensor by contact of the sensor and the passage way's inner wall.

Figure 17:
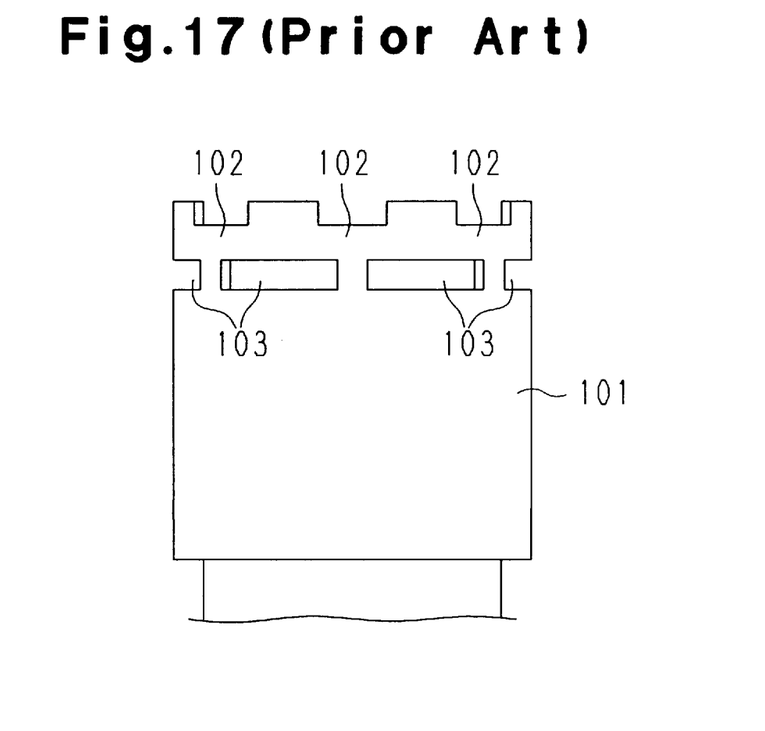
FIG. 17 is a partial diagrammatic side view illustrating a prior art sensor.

Japanese Unexamined Patent Publication No. 6-190050 discloses a medical device having a sensor mounted on the distal end of the tube. The sensor of this publication, which is shown in FIG. 17, includes a flexible tube 101 and a plurality of strain gauges provided on the periphery of the tube's distal end. The tube 101 has a plurality of beams 102 and slits 103 at its distal end. The strain gauges are provided mostly on the beams 102. Contacting the sensor against the inner wall of an intra-corporeal passageway deforms the beams 102. This causes the strain gauges to issue signals in accordance with impedance based on the deformation of the beams 102. The magnitude and the direction of the pressure applied to the tube's distal end are measured based on the signal. The doctor determines the advancing direction of the tube by monitoring the measurement results. Determining the advancing direction of the tube is thus facilitated.

However, since the above described strain gauge type sensor has minuscule beams and slits, the manufacturing of the sensor is complicated. This structure is also disadvantageously large.

Further, having projections and recesses as shown in FIG. 17, the sensor's distal end often gets snagged even when advancing in a straight passageway. This may develop a thrombus in the passageway.

SUMMARY OF THE INVENTION

Accordingly, it is an objective of the present invention to provide a highly biocompatible sensor mounted on an intra-corporeal medical device for detecting the magnitude and the direction of pressure applied to the device's distal end.

A sensor according to the present invention is mounted on the distal end of a medical device. The sensor includes a chip that becomes deformed in accordance with pressure applied thereto and a piezoelectric element that issues detection signals in accordance with the chip's deformation. The pressure is detected based on the issued signals. The sensor also includes a pressure transmitting element mounted distal to the chip. The transmitting element is smaller then the chip and transmits pressure to the chip. The sensor has a cover covering the piezoelectric element and the pressure transmitting element. The cover impart a tapered shape to the device's distal end.

Other aspects and advantages of the invention will become apparent from the following description, taken in conjunction with the accompanying drawings, illustrating by way of example the principals of the invention.

BRIEF DESCRIPTION OF THE DRAWINGS

The invention, together objects and advantages thereof, may best be understood by reference to the following description of the presently preferred embodiments together with the accompanying drawings.

DETAILED DESCRIPTION OF THE PREFERRED EMBODIMENTS

A blood vessel catheter 11 having a sensor according to a first embodiment of the present invention will now be described with reference to FIGS. 1 to 12 and 16.

Figure 16:
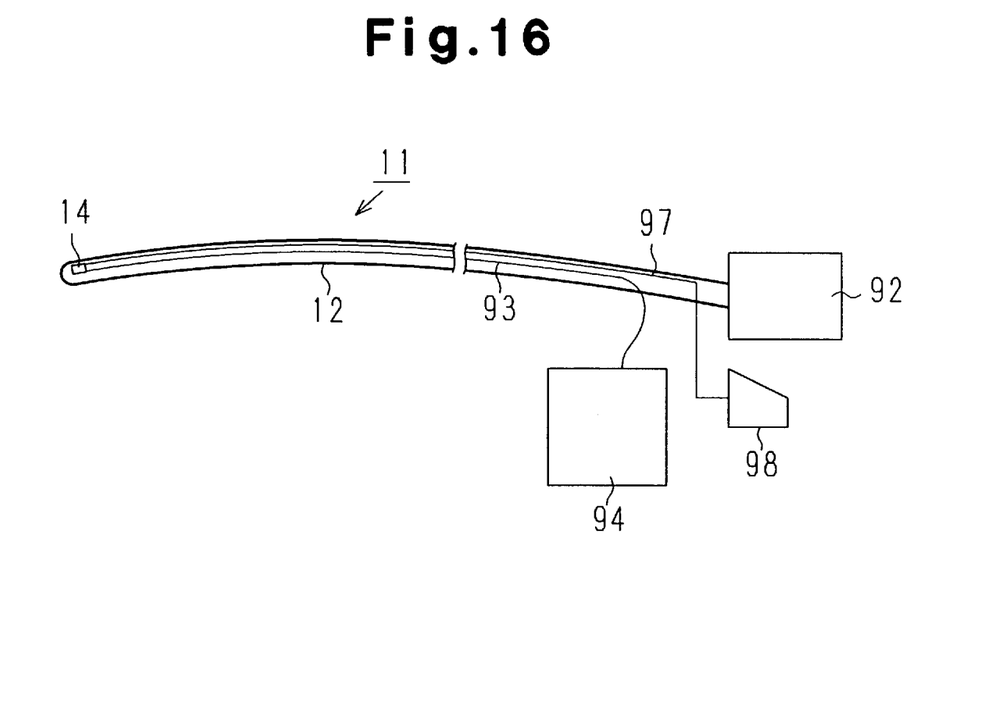
FIG. 16 is a diagrammatic view of a medical catheter.

As shown in FIG. 16, a catheter 11 includes a tube 12 and a manipulator 92 attached to the proximal end of the tube 12. The tube 12 is inserted into a human body, and the manipulator 92 is used to manipulate the tube's movement from outside the body.

The tube 12 has a sensor 14 mounted on its distal end. The sensor 14 detects pressure applied to the distal end of the tube 12. The manipulator 92 includes a plurality of wires (not shown) provided in the tube 12 and a wire controlling device (not shown).

An air compressor 94 is provided at the proximal end of the tube 12. The compressor 94 sends air to an expandable balloon attached to the distal end of the tube 12. An air pipe 93 is connected to the compressor 94 and extends through the tube 12. Sending air into the balloon expands a narrowed blood vessel.

A display device 98 is also provided at the proximal end of the tube 12. The display device 98 displays the results of the sensor's measuring. A cable 97 extends through the tube 12 and connects the sensor 14 and the display device 98.

The doctor manipulates the wire controlling device to bend the distal end of the tube 12, thereby guiding the tube 12 through branched blood vessels. When the distal end of the tube 12, that is, the sensor 14, contacts the vessel's inner wall, the sensor 14 issues signals indicative of the magnitude and the direction of the pressure and transmits the signals to the display device 98. The device 98 displays the results of the sensor's detection.

Figure 1:
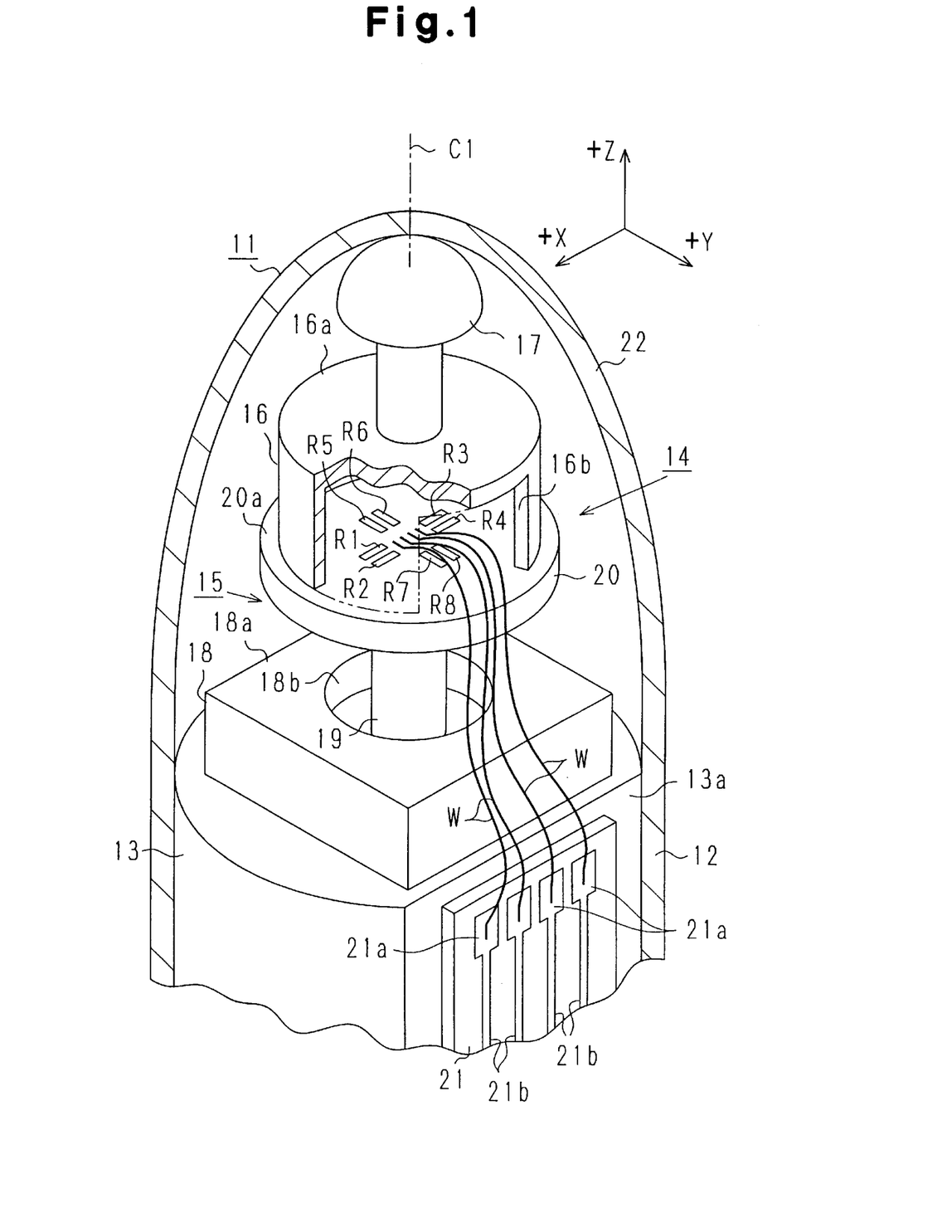
FIG. 1 is a partial diagrammatic perspective view illustrating the distal end of a catheter according to a first embodiment of the present invention.

As shown in FIG. 1, the sensor 14 is covered by the distal end of the silicon rubber tube 12. A substantially cylindrical flexible base 13 is provided in the tube 12. The sensor 14 is mounted on the distal end (upper end in FIG. 1) of the base 13.

Passing the tube 12 through a bend or a branch in a blood vessel applies pressure to the tube 12. The direction of the pressure is different at each bend and branch. Detection signals transmitted from the sensor 14 notify the doctor of the location of branches of vessels, thrombi and the like. Accordingly, the doctor leads the distal end or the tube 12 to the desirable point without relying on his or her instincts.

The sensor 14 includes a sensor chip 15, a cylindrical cap 16 and a projection 17. The axis of the sensor chip 15, the cap 16 and the projection 17 coincide with the axis C1 of the catheter 11. The sensor chip 15 includes a substantially square support plate 18, a cylindrical pole 19 and a disk-like sensing plate 20. A cylindrical recess is formed in the center on the top surface of the plate 18. The pole 19 is vertically provided in the recess. The sensing plate 20 is mounted on the top of the pole 19. The shape of the plate 20 may be a polygon. As shown in FIG. 1, the z-direction is parallel to the axis C1 of the catheter 11. The support plate 18 is secured to the distal end of the base 13 with adhesive. The pole 19 is taller than the top surface 18a of the support plate 18.

Figure 2:
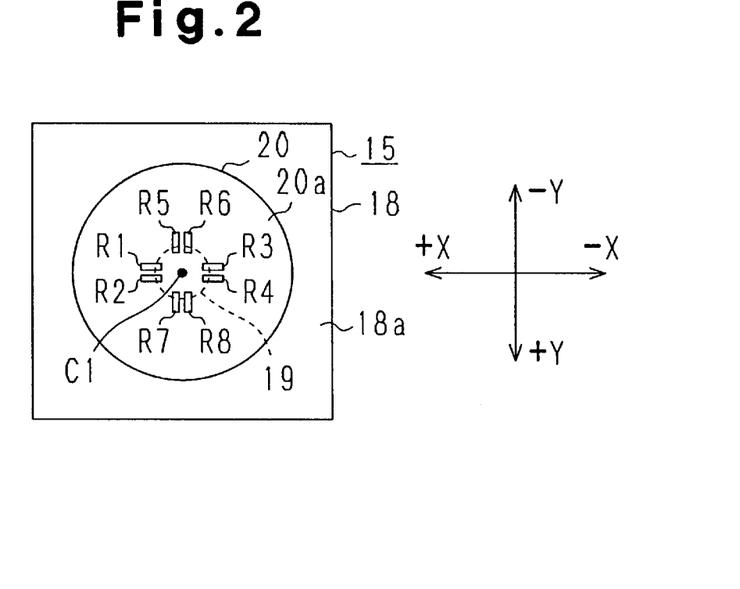
FIG. 2 is a plan view illustrating a layout of strain gauges.

As shown in FIG. 2, eight strain gauges R1 to R8 are integrally formed with the plate 20 on its top surface 20a.

The strain gauges R1 to R8 are perpendicular to the axis C1 of the catheter 11. Specifically, the gauges R1 to R4 are arranged parallel to the x-direction and the gauges R5 to R8 are arranged parallel to the y-direction. A part of each strain gauge R1 to R8 overlaps the distal end of the pole 19. Bending the sensing plate 20 gives great tensile and compression stress to the gauges R1 to R8.

Traces and pads are formed on the top surface 20a of the sensing plate 20 to which the strain gauges R1 to R8 are connected. As shown in FIG. 1, a substrate 21 is attached on the side of the base 13. Pads 21a and traces 21b are formed on the substrate 21. Wires W electrically connect the pads on the plate 20 and the pads 21a on the substrate 21. The substrate 21 is made of flexible material, such as polyimide. The traces 21b are connected to the cable 97 in the tube 12 (see FIG. 16).

The cap 16 covers the strain gauges R1 to R8 on the sensing plate 20. A notch 16b is formed in the side wall of the cap 16. The wires W enter into the cap 16 through the notch 16b.

The projection 17 has a substantially mushroom-like shape and is provided on the top surface 16a of the cap 16. The projection 17 is covered by a flexible cover 22 made of silicon rubber like the tube 12. The tube 12 and the cover 22 may be made of any deformable material such as polyimide and polyurethane.

In the embodiment shown in FIG. 1, the cover 22 is formed by extending the tube 12 to seal the sensor 14. The outer surface of the cover 22 is smoothly formed. Asperities on a catheter may cause thrombi. The catheter 11 of the present invention has no asperities. Therefore the catheter 11 is suitable for usage in blood vessels.

Contacting the distal end of the catheter 11 to the inner wall of a vessel applies pressure to the catheter's distal end. The pressure tilts the projection 17, which is transmitted to the sensing plate 20 via the cap 16. This bends the plate 20 away from the direction of the pressure. The inclination angle of the projection 17 depends on the magnitude of the pressure. Therefore the bending of the plate 20 also depends on the magnitude of the pressure. For example, pressure along the x axis bends the plate 20 in the x-direction and generates tensile or compression stress in the strain gauges R1 to R4, which are arranged parallel to the x axis, in accordance with the pressure. Pressure along the y axis tilts the plate 20 in the y-direction and generates tensile or compression stress in the strain gauges R5 to R8, which are arranged parallel to the y axis in accordance with the pressure.

Specifically, pressure in the positive x-direction tilts the plate 20 to generate tensile stress in the strain gauges R1, R2 and compression stress in the strain gauge R3, R4. Contrarily, pressure in the negative x-direction generates compression stress in the strain gauges R1, R2 and tensile stress in the strain gauges R3, R4.

Similarly, pressure in the positive y-direction tilts the plate 20 to generate tensile stress in the strain gauges R7, R8 and compression stress in the strain gauge R5, R6. Contrarily, pressure in the negative y-direction generates compression stress in the strain gauges R7, R8 and tensile stress in the strain gauges R5, R6.

The individual strain gauges R1 to R8 have the same resistance. Tensile stress in the gauges R1 to R8 increases their resistance and compression stress lowers their resistance. The resistance of the gauges R1 to R8 changes according to the magnitude of the external force. Therefore, measuring the amount of change in the strain gauges' resistance allows the pressure applied to the catheter's distal end to be detected.

The resistance of the strain gauges R1 to R4 changes according to the x axis component of the pressure and the resistance of the strain gauges R5 to R8 changes according to the y axis component of the pressure. Therefore, measuring the changes in the resistance of the strain gauges R1 to R4 and the resistance of the strain gauges R5 to R8 allows the direction of the pressure applied to the catheter's distal end to be detected.

When using the catheter 11, adjusting the catheter's advancing direction in such a way that the pressure detected by the sensor 14 decreases prevents the distal end of the catheter 11 from being pressed against the inner wall of the blood vessel. Guiding the catheter's distal end to the predetermined point is thus facilitated.

Figure 3A:
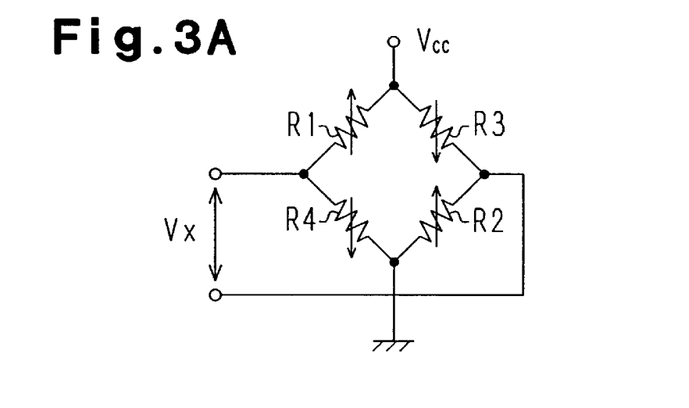
FIG. 3A is a circuit diagram illustrating a set of strain gauges for detecting deformation in x-direction.

As shown in FIG. 3A, the strain gauges R1 to R4 are in a bridge connection. A power source Vcc is applied to the node between the gauges R1 and R3 and the node between the gauges R2 and R4 is grounded. A voltage Vx is outputted from the node between the gauges R1 and R4 and the node between the gauges R2 and R3.

Figure 3B:
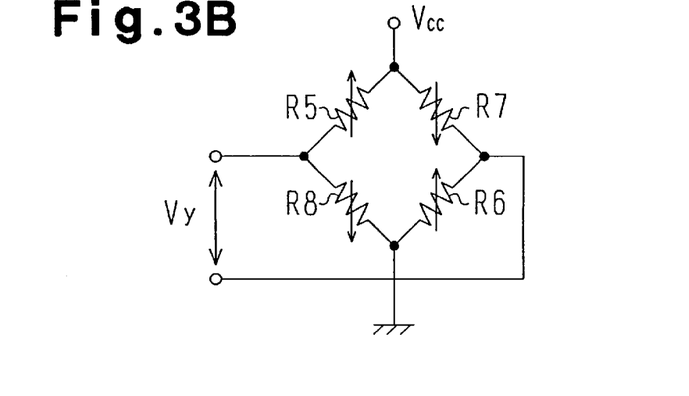
FIG. 3B is a circuit diagram illustrating a set of strain gauges for detecting deformation in y-direction.

As shown in FIG. 3B, the strain gauges R5 to R8 are in a bridge connection. A power source Vcc is applied to the node between the gauges R5 and R7 and the node between the gauges R6 and R8 is grounded. A voltage Vy is outputted from the node between the gauges R5 and R8 and the node between the gauges R6 and R7.

As described above, stress given to the strain gauges R1 to R4 changes the resistance of the gauges R1 to R4. The value of the voltage Vx varies according to the changes in the resistance of the gauges R1 to R4. Similarly, stress given to the strain gauges R5 to R8 changes the resistance of the gauges R5 to R8. The value of the voltage Vy varies according to the changes in the resistance of the gauges R5 to R8.

The manufacturing method of the sensor 14 will now be explained. First steps to manufacture the sensor chip 15 will be explained with reference to the FIGS. 4 to 9.

Each side of the supporting plate 18 of the sensor chip 15 is approximately 1 mm long. A plurality of the sensor chips 15 are formed on a single wafer. FIGS. 4A, 5A, 6A and 7 to 9 are cross-sectional views illustrating a pair of adjacent sensor chips 15 and FIGS. 4B, 5B and 6B are plan views illustrating a single sensor chip 15.

Figure 4A:
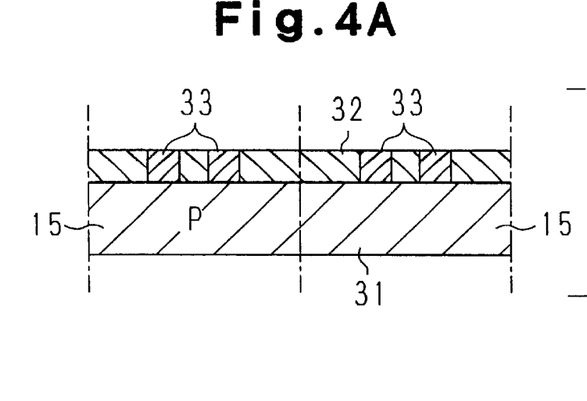
FIG. 4A is a cross-sectional view illustrating a step for manufacturing sensor chips.
Figure 4B:
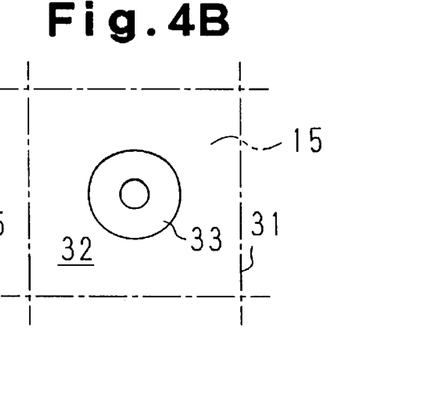
FIG. 4B is a plan view illustrating a step for manufacturing a sensor chip.

As shown in FIGS. 4A and 4B, a first epitaxial growth layer 32 made of N-type single crystal silicon is formed to cover the entire surface of a substrate 31 made of P-type single crystal silicon through vapor phase epitaxy. An oxide film ($SiO_2$ film, not shown) is formed to cover the entire surface of the epitaxial growth layer 32. A doughnut-shaped opening is formed on the oxide film by photo-etching. Next, boron is implanted in the silicon substrate 31 by ion implantation through the doughnut-shaped opening. Thermal diffusion is performed to the implanted boron. This forms a doughnut-shaped first $p^+$ type silicon layer 33 in the first epitaxial growth layer 32. The inner diameter of the first $p^+$ type silicon layer 33 (the diameter of the doughnut's center hole) is equal to the diameter of the pole 19. The oxide film is removed by etching.

Figure 5A:
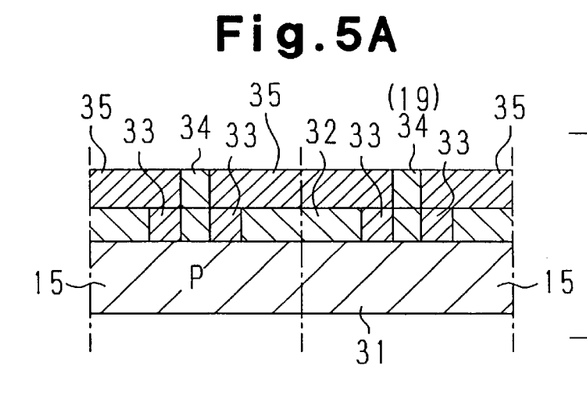
FIG. 5A is a cross-sectional view illustrating a step for manufacturing sensor chips.
Figure 5B:
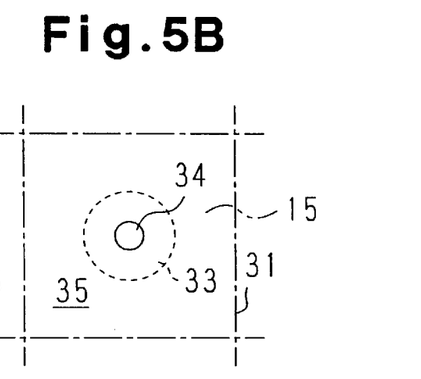
FIG. 5B is a plan view illustrating a step for manufacturing a sensor chip.

Next, as shown in FIG. 5A and 5B, a second epitaxial growth layer 34 made of N-type single crystal silicon is formed to cover the entire surface of the first epitaxial growth layer 32 by vapor phase epitaxy. An oxide film ($SiO_2$ film, not shown) is formed to cover the entire surface of the epitaxial growth layer 34. The oxide film is removed by photo-etching leaving a portion thereof that corresponds to the polo 19. Next, boron is implanted in the silicon substrate 31 by ion implantation. Thermal diffusion is performed to the implanted boron. This forms a second $p^+$ type silicon layer 35 in the second epitaxial growth layer 34. The oxide film is removed by etching.

Figure 6A:
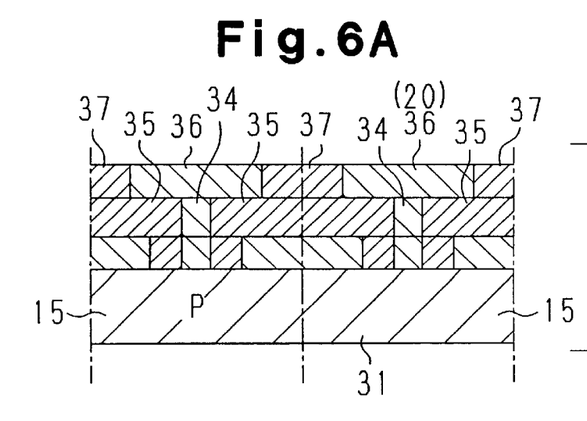
FIG. 6A is a cross-sectional view illustrating a step for manufacturing sensor chips.
Figure 6B:
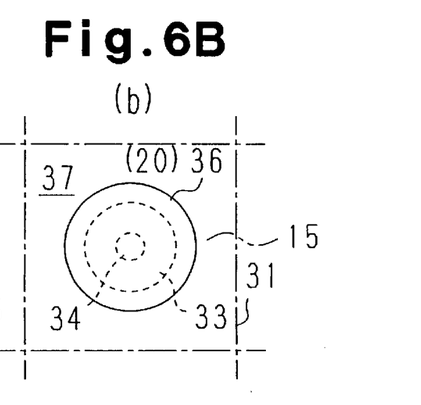
FIG. 6B is a plan view illustrating a step for manufacturing a sensor chip.
Figure 7:
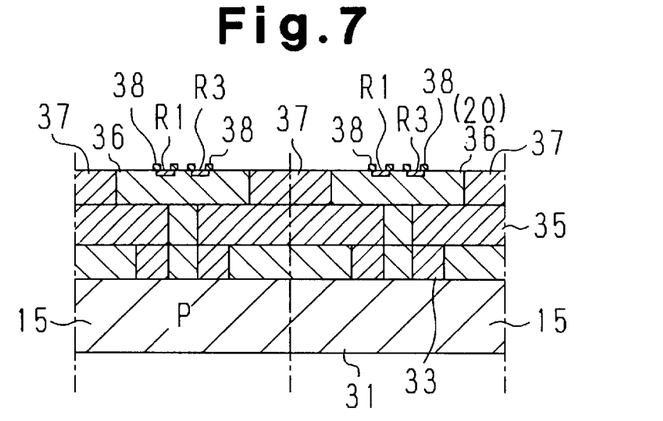
FIG. 7 is a cross-sectional view illustrating a step for manufacturing sensor chips.

Next, as shown in FIG. 6A and 6B, a third epitaxial growth layer 36 made of N-type single crystal silicon is formed to cover the entire surface of the second epitaxial growth layer 34 by vapor phase epitaxy. An oxide film ($SiO_2$ film, not shown) is formed to cover the entire surface of the epitaxial growth layer 36. The oxide film is removed by photo-etching leaving a portion thereof that corresponds to the shape of the sensing plate 20. Next, boron is implanted in the silicon substrate 31 by ion implantation. Thermal diffusion is performed to the implanted boron. This forms a third $p^+$ type silicon layer 37 in the third epitaxial growth layer 37. The oxide film is removed by etching.

The above described steps form first, second and third $p^+$ type silicon layers 33, 35 and 37 that include the part corresponding to the space around the pole 19 and the sensing plate 20. Etching the first, second and third $p^+$ type silicon layers 33, 35 and 37 according to the method described below forms the pole 19 and the sensing board 20.

A mask (not shown) is formed on the third epitaxial growth layer 36. Openings are formed on predetermined region on the mask. Next, boron is implanted in the epitaxial growth layer 36 by ion implantation. Thermal diffusion is performed on the implanted boron. This forms the stain gauges R1 to R8 on a region corresponding to the surface of the sensing plate 20. Then, the mask is removed.

After performing sputtering or vacuum deposition of aluminum on the third epitaxial growth layer 36, photolithography is performed on the layer 36 to form traces 38. The traces 38 are shown only in FIGS. 7 to 9 to avoid complexity in the other drawings.

Figure 9:
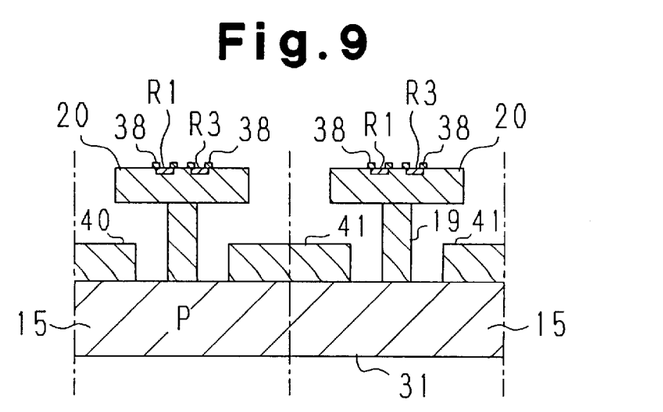
FIG. 9 is a cross-sectional view illustrating a step for manufacturing sensor chips.

A passivation film (not shown) is formed on the entire surface of the third epitaxial growth layer 36 by accumulating molecules of SiN or $Si_3N_4$ through chemical-vapor deposition (CVD) or the like, Etching resist 39 is formed to cover the entire surface of the silicon substrate 31. Part of the resist 39 is removed by photolithography to expose the surface of the third $p^+$ type silicon layer 37. Next, anodic oxidation is performed to the silicon substrate 31. Anodic oxidation is a process in which the substrate 31 is used as an anode in an electrolyte and current between the anode and a cathode forms porous Si, $SiO_2$ or porous $Al_2O_3$. Hydrofluoric acid aqueous solution is used as the electrolyte in this embodiment. The anodic oxidation selectively changes the first, second and third $p^+$ silicon layer 33, 35 and 37 to a porous silicon layer 40.

Then, alkali etching is performed with tetramethyl ammonium hydroxide (TMAH) to selectively etch the porous silicon layer 40. The porous silicon layer 40 is more solvable with alkali than other parts on which anodic oxidation was not performed. The difference in etching speeds removes the porous silicon layer 40 leaving the pole 19 and the sensing plate 20.

The remainder of the first epitaxial growth layer 32 around the pole 19 serves as a stopper to protect the pole 19 and the sensing plate 20. An excessive pressure applied to the distal end of the catheter 11 tilts the plate 20 and the pole 19 and cause them to contact the stopper 41. In this manner, the stopper 41 limits the tilting of the plate 20 and the pole 19 to protect them.

Figure 8:
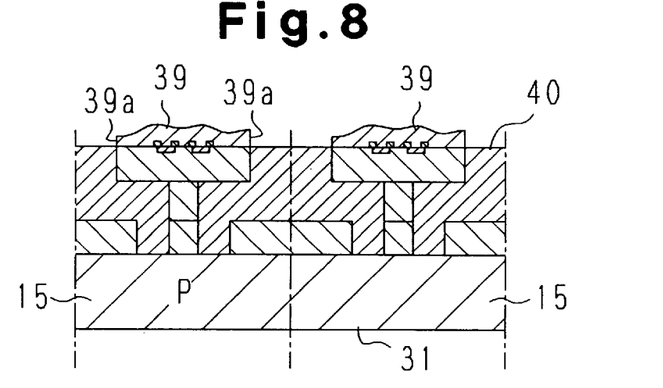
FIG. 8 is a cross-sectional view illustrating a step for manufacturing sensor chips.

Finally, the etching resist in FIG. 8 is removed and the sensor chip 15 is cut away from the substrate 31 through dicing. An described above, the senor chip 15 is easily manufactured using typical steps to manufacture semiconductors. Further, forming a plurality of sensor chips 15 on a single silicon substrate 31 simultaneously reduces the manufacturing cost of the sensor chips 15.

Figure 10:
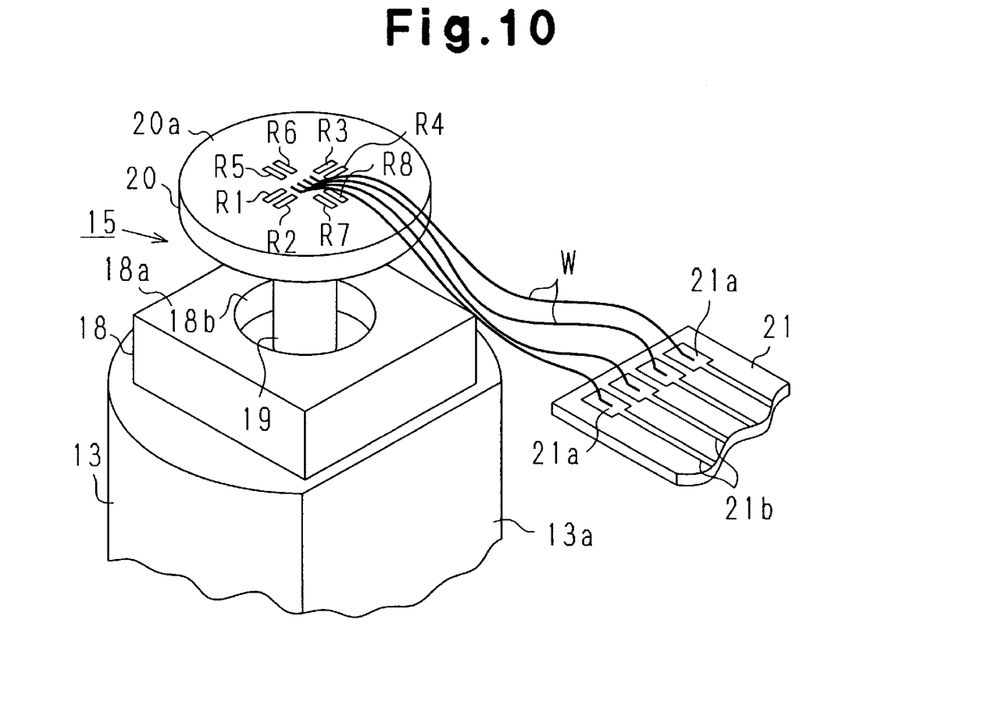
FIG. 10 is a partial diagrammatic perspective view illustrating a step for assembling a sensor.

The sensor chip 15, which is manufactured in the above manner, is adhered to the base 13. Then, the substrate 21 held by a jig (not shown) is positioned close to the sensor chip 15. The pads 21a formed on the substrate 21 and the chip 15 are bonded by the wires W.

Figure 11:
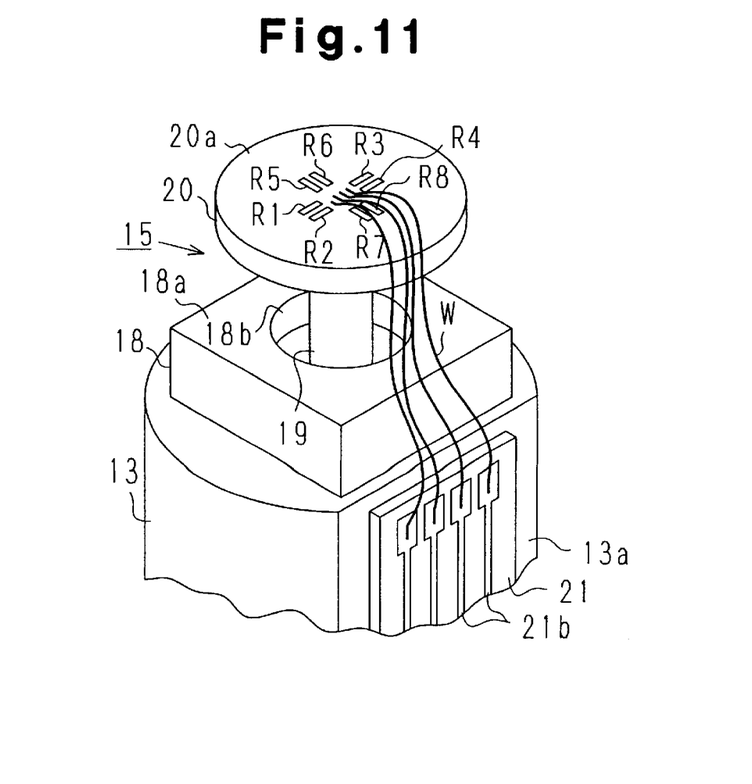
FIG. 11 is a partial diagrammatic perspective view illustrating a step for assembling a sensor.

Next, as shown in FIG. 11, the substrate 21 is adhered to the flat portion 13a of the base 13. In the above method, bonding of the wires W is easier than in a method in which both the sensor chip 15 and the substrate 21 are fixed to the base 13 before bonding with the wires W.

Figure 12:
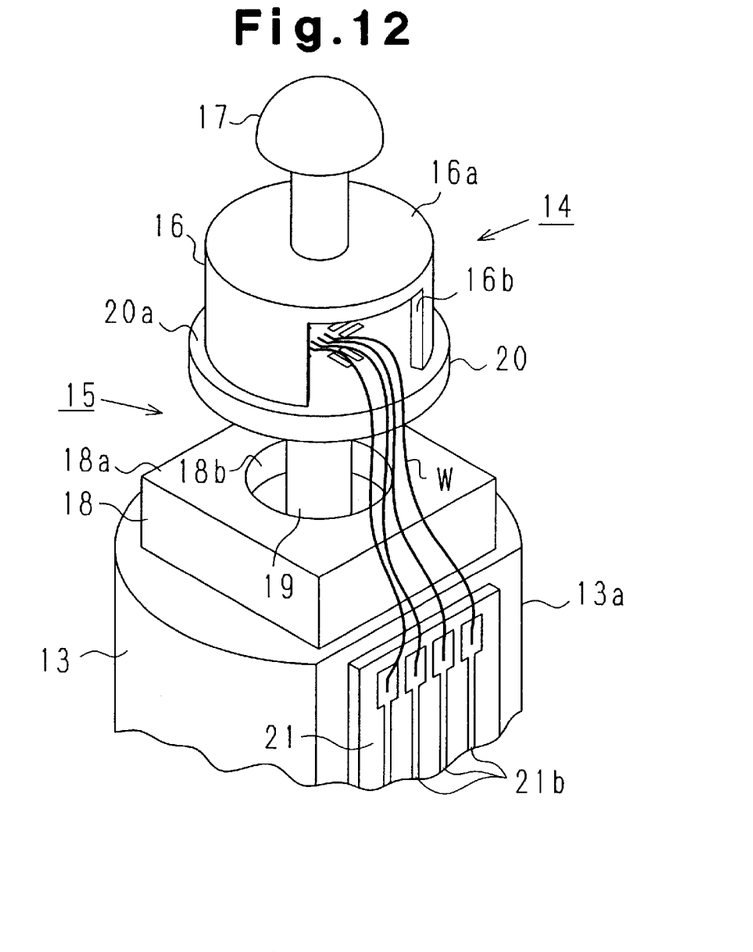
FIG. 12 is a partial diagrammatic perspective view illustrating a step for assembling a sensor.

As shown in FIG. 12, the cap 16 with the projection 17 previously attached to its top surface 16a is attached to the top surface 20a of the sensing plate 20. Covering the assembled parts with the cover 22 shown in FIG. 1 completes the mounting of the sensor 14 on the distal end of the catheter 11.

Instead of forming the strain gauges R1 to R8, a chip incorporating strain gauges may be mounted on the top surface 20a of the sensing plate 20.

The cap 16 and the projection 17 may be integrally formed. Further, a substantially dome-shaped cap may be used so that the protection 17 can be omitted.

In the above embodiment, boron is used to form the first, second and third p+ silicon layers 33, 35 and 37.

However, other p-type impurities such as gallium (Ga) may be used for this purpose.

The present invention is embodied in the blood vessel catheter 11. The sensor 14 may be further employed in other types of medical devices inserted in an intestinum crassum, an intestinum tenue, a duodenum, other digestive tubes, a urethra, a uterine tube, lymphoduct, bile tube, a vagina, an acoustic meatus, a cavum nasi, an esophagus and bronchia. The sensor 14 of the present invention may be employed not only in the externally controlled catheter 11 but also may be provided at the distal end of a mobile medical device employing micro machine technology. Further, the sensor 14 may be employed not only for devices for human bodies but also for devices for animal bodies.

A second embodiment according to the present invention will now be described with reference with FIGS. 13 to 15. To avoid a redundant description, like or same reference numerals are given to those components that are the same as the corresponding components of the first embodiment.

In the second embodiment, the number of strain gauges is different from the number of the strain gauges in the first embodiment. As shown in FIG. 13, the sensing plate 20 has a pair of strain gauges R11, R13 extending parallel to the axis X and a pair of strain gauges R12, R13 extending parallel to the axis Y.

Figure 14A:
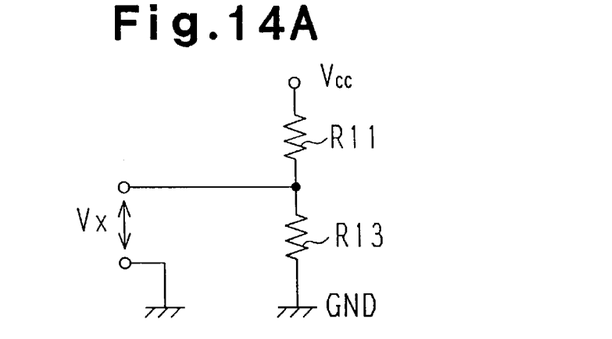
FIG. 14A is a circuit diagram illustrating the strain gauges of FIG. 13 for detecting deformation in x-direction.

As shown in FIG. 14A, the strain gauges R11, R13 are connected in series between the power supply Vcc and the ground GND. The voltage Vx between the node between the strain gauges R11, R13 and the ground GND is outputted. As shown in FIG. 14B, the strain gauges R12, R14 are connected in series between the power supply Vcc and the ground GND. The voltage Vy between the node between the strain gauges R12, R14 and the ground GND is outputted. This structure allows, as in the first embodiment, pressure applied to the distal end of the catheter 11 to be detected as the voltage Vx corresponding to the x axis component of the pressure and the voltage Vy corresponding to y axis component of the pressure.

Figure 13:
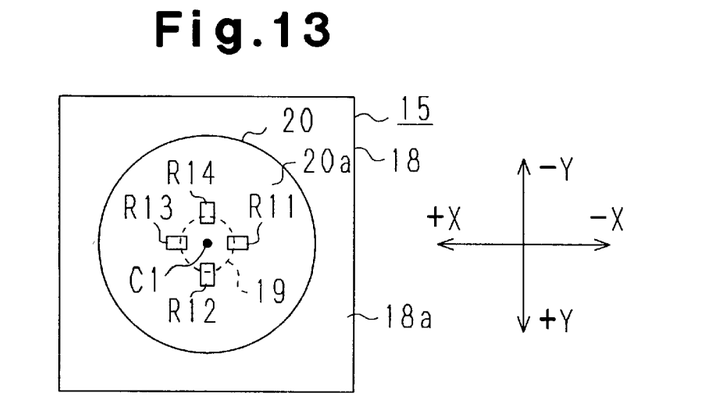
FIG. 13 is plan view of a sensor chip illustrating the layout of another set of strain gauges.
Figure 14B:
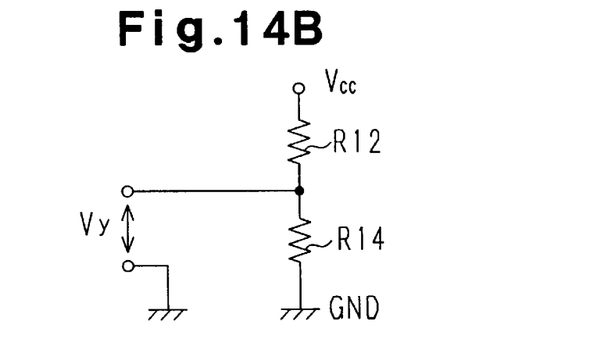
FIG. 14B is a circuit diagram illustrating the strain gauges of FIG. 13 for detecting deformation in y-direction.
Figure 15A:
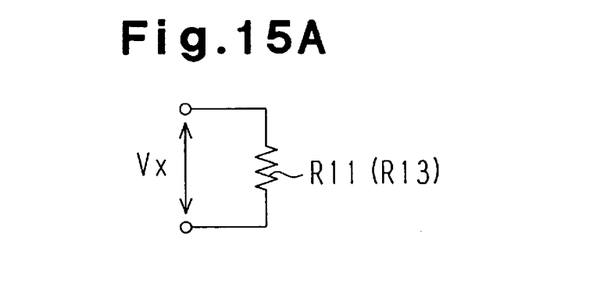
FIG. 15A is a circuit diagram illustrating yet another strain gauge for detecting deformation in x-direction.
Figure 15B:
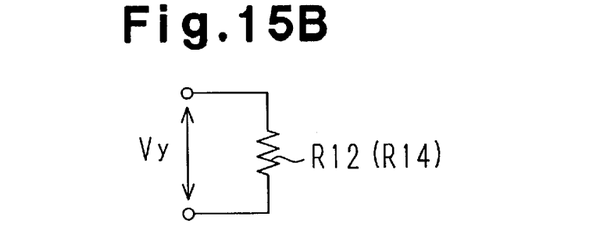
FIG. 15B is a circuit diagram illustrating yet another strain gauge for detecting deformation in y-direction.

In an embodiment shown in FIGS. 15A and 15B, the strain gauges R11, R12, R13 and R14 are arranged as shown in FIG. 13. A predetermined current is constantly passed through the individual gauges R11 to R14. When the resistance of each gauge changes in accordance with its deformation, measuring the voltages Vx, Vy between the ends of each gauge allows the pressure applied to the sensor 14 to be detected.

Although several embodiment of the present invention have been described herein, it should be apparent to those skilled in the art that the present invention may be embodied in many other specific forms without departing from the spirit or scope of the invention.

Therefore, the present examples and embodiments are to be considered as illustrative and not restrictive and the invention is not to be limited to the details given herein, but may be modified within the scope and equivalence of the appended claims.

What is claimed is:

1. A sensor attached to a distal end of an intra-corporeal medical device for guiding the medical device by detecting forces applied thereto when the distal end contacts an intra-corporeal tissue, said sensor comprising:
    a chip deformable in accordance with the forces;
    a plurality of strain gauges located on said chip for issuing signals corresponding to said deformation of the chip, wherein said forces are detected in accordance with said signals;
    a force transmitter attached to the distal end of the device at a location more distal than said chip for transmitting said forces to said chip; and
    a cover that covers said chip, strain gauges and force transmitter and that gives a tapered shape to said distal end, wherein said chip comprises:
        a base located at said distal end of the device;
        a pole standing on said base; and
        a sensing plate attached to a distal end of said pole, wherein said strain gauges are provided on said sensing plate.

2. The sensor according to claim 1, wherein said strain gauges are located on a surface of said chip, and wherein said force transmitter includes a cap attached to said chip for covering said strain gauges and a projection extending distally from said cap, wherein said projection is acted upon by said forces.

3. The sensor according to claim 1, wherein one of said strain gauges is placed in alignment with a first axis and another of said strain gauges is placed in alignment with a second axis that is orthogonal to said first axis.

4. The sensor according to claim 3, wherein said base is provided with a side face and a substrate that is electrically connected to an external device is attached to said side face, wherein said substrate and said chip are connected by a wire.

5. The sensor according to claim 3, wherein said sensor is provided with eight strain gauges, wherein first, second, third and fourth of said eight strain gauges are placed in alignment with said first axis, and wherein fifth, sixth, seventh and eighth of said eight strain gauges are placed in alignment with said second axis.

6. The sensor according to claim 3, wherein said sensor is provided with four strain gauges, wherein first and second of said four strain gauges are placed in alignment with said first axis, and wherein third and fourth of said four strain gauges are placed in alignment with said second axis.

7. The sensor according to claim 1, wherein said cover is flexible.

8. The sensor according to claim 1, wherein said chip further comprises a stopper for limiting the deflection of said sensing plate and pole.

9. The sensor according to claim 1, wherein said chip is formed by forming epitaxial growth layer made of single crystal silicon on a silicon substrate, forming a p$^+$ silicon layer within a predetermined region of said epitaxial growth layer, changing said p$^+$ silicon layer into a porous silicon layer by anodic oxidation, and selectively etching said porous silicon layer.

10. The sensor according to claim 1, wherein the device includes a catheter.

11. The sensor according to claim 10, wherein said catheter is covered with a tube and wherein said cover is formed by extending said tube and by closing its distal end.

12. The sensor according to claim 1, wherein the surface of said cover is smooth.

13. A sensor attached to a distal end of an intra-corporeal medical device for guiding the medical device by detecting forces applied thereto when the distal end contacts an intra-corporeal tissue, said sensor comprising:
   a generally planar chip deformable in accordance with the forces;
   a plurality of strain gauges located on said chip for issuing variable signals corresponding to said deformation of the chip, wherein said forces are detected in accordance with said signals;
   a force transmitter attached to the distal end of the device at a location more distal than said chip for transmitting said forces to said chip, wherein said force transmitter has a longitudinal axis that extends perpendicular to the plane of said chip; and
   a smooth cover that covers said chip, strain gauges and force transmitter, wherein said chip comprises:
   a base located at the distal end of the device;
   a pole standing on said base;
   a sensing plate attached to a distal end of said pole; and, wherein said strain gauges are provided on a surface of said sensing plate.

14. The sensor according to claim 13, wherein said strain gauges are located on a surface of said chip that faces said force transmitter, and wherein said force transmitter is connected to peripheral parts of said chip.

15. The sensor according to claim 13, wherein one of said strain gauges is placed in alignment with a first axis to detect forces aligned with the first axis and a second one of said strain gauges is placed in alignment with a second axis orthogonal to said first axis to detect forces aligned with the second axis.

16. A sensor attached to a distal end of an intra-corporeal medical device for detecting forces applied thereto, said sensor comprising:
   a chip deformable in accordance with the forces;
   a plurality of strain gauges located on said chip for issuing signals corresponding to said deformation of the chip, wherein said forces are detected in accordance with said signals;
   a force transmitter attached to the distal end of the device at a location more distal than said chip for transmitting said forces to said chip; and
   a cover that covers said chip, strain gauges and force transmitter and that gives a tapered shape to said distal end and wherein said chip comprises:
   a base located at said distal end of the device;
   a pole standing on said base; and
   a sensing plate attached to a distal end of said pole, wherein said strain gauges are provided on said sensing plate.

17. The sensor according to claim 16, wherein one of said strain gauges is placed in alignment with a first axis and another of said strain gauges is placed in alignment with a second axis that is orthogonal to said first axis.

18. The sensor according to claim 17, wherein said base is provided with a side face and a substrate that is electrically connected to an external device is attached to said side face, wherein said substrate and said chip are connected by a wire.

19. The sensor according to claim 17, wherein said sensor is provided with eight strain gauges, wherein first, second, third and fourth of said eight strain gauges are placed in alignment with said first axis, and wherein fifth, sixth, seventh and eighth of said eight strain gauges are placed in alignment with said second axis.

20. The sensor according to claim 17, wherein said sensor is provided with four strain gauges, wherein first and second of said four strain gauges are placed in alignment with said first axis, and wherein third and fourth of said four strain gauges are placed in alignment with said second axis.

21. The sensor according to claim 16, wherein said chip further comprises a stopper for limiting the deflection of said sensing plate and pole.

22. The sensor according to claim 16, wherein said chip is formed by forming epitaxial growth layer made of single crystal silicon on said silicon substrate, forming a p$^+$ silicon layer within a predetermined region of said epitaxial growth layer, changing said p$^+$ silicon layer into a porous silicon layer by anodic oxidation, and selectively etching said porous silicon layer.

23. The sensor according to claim 16, wherein the device includes a catheter.

24. The sensor according to claim 23, wherein said catheter is covered with a tube and wherein said cover is formed by extending said tube and by closing its distal end.

25. A sensor attached to a distal end of an intra-corporeal medical device for detecting forces applied thereto, said sensor comprising:
   a generally planar chip deformable in accordance with the forces;
   a plurality of strain gauges located on said chip for issuing variable signals corresponding to said deformation of the chip, wherein said forces are detected in accordance with said signals;
   a force transmitter attached to the distal end of the device at a location more distal than said chip for transmitting said forces to said chip, wherein said force transmitter has a longitudinal axis that extends perpendicular to the plane of said chip; and
   a smooth cover that covers said chip, strain gauges and force transmitter, wherein said chip comprises:
   a base located at the distal end of the device;
   a pole standing on said base; and
   a sensing plate attached to a distal end of said pole; and, wherein said strain gauges are provided on a surface of said sensing plate.

26. A sensor attached to a distal end of an intra-corporeal medical device for detecting forces applied thereto, said sensor comprising:
   a generally planar chip deformable in accordance with the forces;
   a plurality of strain gauges located on said chip for issuing variable signals corresponding to said deformation of the chip, wherein said forces are detected in accordance with said signals;

a force transmitter attached to the distal end of the device at a location more distal than said chip for transmitting said forces to said chip, wherein said force transmitter has a longitudinal axis that extends perpendicular to the plane of said chip; and a smooth cover that covers said chip, strain gauges and force transmitter, wherein one of said strain gauges is placed in alignment with a first axis to detect forces aligned with the first axis and a second one of said strain gauges is placed in alignment with a second axis orthogonal to said first axis to detect forces aligned with the second axis.

27. A sensor attached to a distal end of an intra-corporeal medical device for guiding the medical device by detecting forces applied thereto when the distal end contacts an intra-corporeal tissue, said sensor comprising:

generally planar chip deformable in accordance with the forces;

plurality of strain gauges located on said chip for issuing variable signals corresponding to said deformation of the chip, wherein said forces are detected in accordance with said signals;

a force transmitter attached to the distal end of the device at a location more distal than said chip for transmitting said forces to said chip, wherein said force transmitter has a longitudinal axis that extends perpendicular to the plane of said chip; and a smooth cover that covers said chip, strain gauges and force transmitter, wherein one of said strain gauges is placed in alignment with a first axis to detect forces aligned with the first axis and a second one of said strain gauges is placed in alignment with a second axis orthogonal to said first axis to detect forces aligned with the second axis.

28. The sensor according to claim 27, wherein said strain gauges are located on a surface of said chip that faces said force transmitter, and wherein said force transmitter is connected to peripheral parts of said chip.

29. The sensor according to claim 27, wherein said chip comprises:

a base located at the distal end of the device;

a pole standing on said base;

a sensing plate attached to a distal end of said pole; and, wherein said strain gauges are provided on a surface of said sensing plate.

* * * * *